US011135208B2

(12) United States Patent
Wehrung et al.

(10) Patent No.: US 11,135,208 B2
(45) Date of Patent: Oct. 5, 2021

(54) 1,4-DIHYDROPYRIDINE COMPOSITIONS, METHODS OF MAKING AND USE

(71) Applicant: American Regent, Inc., Shirley, NY (US)

(72) Inventors: Daniel Walter Wehrung, Johnstown, OH (US); Meng Zhong, Westerville, OH (US); Saral Pinkal Patel, Powell, OH (US); Bindhu Madhavi Rayaprolu, Columbus, OH (US)

(73) Assignee: American Regent, Inc., Shirley, NY (US)

( * ) Notice: Subject to any disclaimer, the term of this patent is extended or adjusted under 35 U.S.C. 154(b) by 0 days.

(21) Appl. No.: 16/815,776

(22) Filed: Mar. 11, 2020

(65) Prior Publication Data

US 2021/0046062 A1 Feb. 18, 2021

Related U.S. Application Data

(60) Provisional application No. 62/885,704, filed on Aug. 12, 2019.

(51) Int. Cl.
*A61K 31/4422* (2006.01)
*A61K 47/18* (2017.01)

(52) U.S. Cl.
CPC ........ *A61K 31/4422* (2013.01); *A61K 47/183* (2013.01)

(58) Field of Classification Search
CPC .......................... A61K 31/4422; A61K 47/183
USPC ........................................................ 514/356
See application file for complete search history.

(56) References Cited

U.S. PATENT DOCUMENTS

| | | | |
|---|---|---|---|
| 3,985,758 A | 10/1976 | Murakami et al. | |
| 5,164,405 A * | 11/1992 | McFarlane | A61K 9/0019 514/354 |
| 5,198,226 A | 3/1993 | MacFarlane et al. | |
| 6,265,392 B1 | 7/2001 | Abrahamson et al. | |
| 7,612,102 B2 | 11/2009 | Duncan et al. | |
| 7,659,291 B2 | 2/2010 | Duncan et al. | |
| 9,549,994 B2 | 1/2017 | Gupta et al. | |
| 10,478,453 B1 | 11/2019 | Maloney et al. | |
| 2007/0112041 A1* | 5/2007 | Bhowmick | A61K 9/0019 514/355 |
| 2010/0022602 A1 | 1/2010 | Gupta et al. | |
| 2012/0214761 A1 | 8/2012 | Gupta et al. | |
| 2014/0206643 A1 | 7/2014 | Gupta et al. | |
| 2017/0247460 A1* | 8/2017 | Geiger | A61P 3/10 |

FOREIGN PATENT DOCUMENTS

| | | | |
|---|---|---|---|
| CN | 102 397 245 A | | 4/2012 |
| CN | 102397245 A | * | 4/2012 |
| CN | 105079010 A | * | 11/2015 |
| GB | 2 228 412 A | | 8/1990 |
| RU | 2013 133938 A | | 1/2015 |
| WO | 2012/051116 A1 | | 4/2012 |
| WO | 2014/178065 A1 | | 11/2014 |
| WO | 2017/117268 A1 | | 7/2017 |

OTHER PUBLICATIONS

CN-102397245-A machine translation (Year: 2012).*
CN-105079010-A machine translation (Year: 2015).*
PubChem1 https://pubchem.ncbi.nlm.nih.gov/compound/Sorbitol (Year: 2020).*
PubChem2 https://pubchem.ncbi.nlm.nih.gov/compound/Citric-acid-monohydrate (Year: 2020).*
"Chapter IV Nicardipine Injection Method Development and Method Validation," retrieved from the Internet on Mar. 10, 2020 from URL: https://shodhganga.inflibnet.ac.in/bitstream/10603/19305/14/14_chapter-iv%20nicardipine%20injection%20method%20development%20and%20method%20validation.pdf.
Cataldi, M. and Bruno, F. "1,4 Dihydropyridines: The Multiple Personalities of a Blockbuster Drug Family," Translational Medicine @ UniSa, ISSN 2239-9747, 2012, 4(2): 12-26.
"Therapeutic Class Overview Calcium-Channel Blocking Agents (Dihydropyridines)," University of Massachusetts Medical School, 2016, pp. 1-5.
Cardene IV prescribing information package insert, EKR Therapeutics, Inc., Jan. 2019, 8 pages.
Bhupendrasinh, K. V., et al. "Identification and Characterization of a Novel Potential Degradant and Development and Validation of Stability-Indicating RP-LC Method for Nicardipine Impurities in Injectable Dosage Form," Journal of Liquid Chromatography & Related Technologies, vol. 36, 2013, Issue 15, pp. 2166-2181, Abstract.
Bonferoni, M.C., et al. "Photostability evaluation of nicardipine HCI solutions," International Journal of Pharmaceutics, vol. 80 (1992) p. 109-117.
Baranda, Ana B., et al. "Instability of calcium channel antagonists during sample preparation for LC-MS-MS analysis of serum samples," Forensic Science International, vol. 156 (2006) pp. 23-24.
Shudo, Norimasa, et al. "Two Pyridine Analogues with More Effective Ability to Reverse Multidrug Resistance and with Lower Calcium Channel Blocking Activity Than Their Dihydropyridine Counterparts," Cancer Research. vol. 50, pp. 3055-3061, May 15, 1990.

(Continued)

*Primary Examiner* — Yevgeny Valenrod
(74) *Attorney, Agent, or Firm* — Sorell, Lenna & Schmidt, LLP; William D. Schmidt, Esq.

(57) ABSTRACT

Provided herein are pharmaceutical compositions comprising a class of calcium channel blockers and at least one chelating agent. More specifically, the pharmaceutical compositions comprise at least one 1,4-dihydropyridine (DHP) compound and at least one chelating agent. The chelating agents used in this disclosure can decrease the degradation of the constituent DHPs of the DHP compositions. The DHP compositions can be used to treat cardiovascular disorders and are more stable for prolonged periods of time.

30 Claims, No Drawings

(56) References Cited

OTHER PUBLICATIONS

Committee for Proprietary Medicinal Products (CPMP), "Note for Guidance on Excipients, Antioxidants and Antimicrobial Preservatives in the Dossier for Application for Marketing Authorisation of a Medicinal Product," The European Agency for the Evaluation of Medicinal Products, Evaluation of Medicines for Human Use, London, Feb. 20, 2003.
Mozziconacci, O., et al. "Metal-Catalyzed Oxidation of Protein Methionine Residues in Human Parathyroid Hormone (1-34): Formation of Homocysteine and a Novel Methionine-Dependent Hydrolysis Reaction," Mol Pharm. Feb. 4, 2013; 10(2): 739-755. doi:10.1021/mp300563m.
Gutteridge, John M.C., "Ferrous ion-EDTA-stimulated phospholipid peroxidation—A reaction changing from alkoxyl-radical- to hydroxyl-radical-dependent initiation," Biochem. J. (1984) vol. 224, pp. 697-701.
"5.1.3 Efficacy of Antimicrobial Preservation," European Pharmacopoeia 7.0, Jan. 2011, retrieved from the Internet on Mar. 11, 2020 at url: https://www.drugfuture.com/Pharmacopoeia/EP7/DATA/50103E.PDF.
"Microbial Tests (51) Antimicrobial Effectiveness Testing" The United States Pharmacopeial Convention, 2011, retrieved from the Internet on Mar. 11, 2020 at url: https://www.drugfuture.com/Pharmacopoeia/usp35/PDF/0052-0054%20%5B51%5D%20ANTIMICROBIAL%20EFFECTIVENESS%20TESTING.pdf.
International Search Report and Written Opinion of the International Searching Authority (ISA/EPO) dated Nov. 13, 2020 in corresponding International Application No. PCT/US2020/045758 filed Aug. 11, 2020.
A translation of Tables 2 and 3 from Chinese Patent Publication No. CN 102397245 A (Apr. 4, 2012).
Exhibit B. Andersson, Maria M., et al. Stabilizing effect of chemical additives against oxidation of lactate dehydrogenase. Biotechnol. Appl. Biochem. (2000) vol. 32, pp. 145-153.
Exhibit C. Ji, Junyan A., et al. Biotechnology. Mehtionine, Tryptophan, and Histidine Oxidation in a Model Protein, PTH: Mechanisms and Stabilization. J Pharm Sci, Dec. 2009 vol. 98, No. 12., pp. 4485-4500.
Exhibit D. Bee, Jared S., et al. Precipitation of a Monoclonal Antibody by Soluble Tungsten. J Pharm Sci. Sep. 2009, vol. 98, No. 9, pp. 3290-3301.
Exhibit E. Mozziconacci, O., et al. Metal-Catalyzed Oxidation of Protein Methionine Residues in Human Parathyroid Hormone (1-34): Formation of Homocysteine and a Novel Methionine-Dependent Hydrolysis Reaction. Mol Pharm. Feb. 4, 2013; 10(2): 739-755.

\* cited by examiner

1,4-DIHYDROPYRIDINE COMPOSITIONS, METHODS OF MAKING AND USE

CROSS-REFERENCE TO RELATED APPLICATION

This application claims priority from provisional application No. 62/885,704, filed on Aug. 12, 2019, the entire disclosure of which is hereby incorporated by reference in its entirety.

TECHNICAL FIELD

Provided herein are improved pharmaceutical compositions comprising 1,4-dihydropyridines ("DHPs"), a class of calcium channel blockers, and at least one chelating agent.

Pharmaceutical products containing DHP active ingredients exist in various dosage forms and are used to treat a variety of cardiovascular disorders including hypertension, coronary artery disease, angina, arrhythmia and blood circulatory conditions.

BACKGROUND

It has been reported that calcium channel blockers are amongst the most successful drugs ever used by humans. See generally Cataldi, M. et al., 1, 4-Dihydropyridines: The Multiple Personalities of a Blockbuster Drug Family, Translational Medicine @ UniSa,—ISSN 2239-9747 (2012) 4 (2) 12-26. However, a class of calcium channel blockers, namely 1,4-dihydropyridines ("DHPs"), are susceptible to oxidation of the dihydropyridine ring to the pyridine ring, forming resonance-stabilized, pyridine analogues. See Bonferoni M. C. et al., Photostability evaluation of Nicardipine HCl Solutions, International Journal of Pharmaceuticals, 80 (1992) 109-117. These pyridine analogues are considered impurities as they possess considerably lower calcium channel blocking activity than their dihydropyridine forms, leading to decreased therapeutic effects and the increase of potential toxicological effects. See Baranda A. B. et al., Instability of Calcium channel antagonists during sample preparation for LC-MS-MS analysis of serum samples, Forensic Science International, 156 (2006) 23-34; Norimasa S. et al., Two pyridine analogues with more effective ability to reverse multidrug resistance and with lower calcium channel blocking activity than their dihydropyridine counterparts, Cancer Research, 50 (1990) 3055-3061.

As summarized in Table 1, there have been multiple product recalls of pharmaceutical products containing the calcium channel blocker nicardipine hydrochloride ((±)-2-(benzyl-methyl amino) ethyl methyl 1,4-dihydro-2,6-dimethyl-4-(m-nitrophenyl)-3,5-pyridinedicarboxylate monohydrochloride).

TABLE 1

Nicardipine Hydrochloride Product Recalls[1]

| Product | Dosage Form | Strength | Manufacturer | FDA Recall # | Reason |
|---|---|---|---|---|---|
| Cardene ®[2] | Capsule | 30 mg | PDL Biopharma, Inc. | D-844-2009 | Unknown |
| Cardene ®[2] | Capsule | 30 mg | PDL Biopharma, Inc. | D-1909-2009 | Unknown |
| Nicardipine Hydrochloride Injection | Injection | 25 mg/ 10 mL | TEVA Pharmaceuticals, Inc. | D-167-2009 | Exceeded impurity specification |
| Nicardipine Hydrochloride Injection | Injection | 25 mg/ 10 mL | Hikma Pharmaceuticals, Inc. | D-691-2013 | Failed Impurity/ Degradation Specifications/Exceed specification for Nitrophenyl Pyridine Derivative impurity |
| Nicardipine Hydrochloride | Capsule | 20 mg | Mylan Pharmaceuticals, Inc. | D-032-2012 | Unknown |
| Nicardipine Hydrochloride | Capsule | 30 mg | Mylan Pharmaceuticals, Inc. | D-033-2012 | Unknown |
| Nicardipine Hydrochloride Injection | Injection | 25 mg/ 10 mL | Mylan Pharmaceuticals, Inc. | N/A | Sub-potent Drug and failed impurities/ degradation specifications |

[1]Information obtained through FDA Recall and Safety Alert Database.
[2]Cardene ® is a registered U.S. trademark of EKR Therapeutics, Inc.

For the recalls with known reasons, those recalls were related to products that failed impurity specifications. Those failures were attributable, at least in part, to the degradation of the active pharmaceutical ingredients. Accordingly, there is a need for pharmaceutical compositions comprising DHPs which are more stable for prolonged periods of time.

The compositions provided herein address these and other needs by providing a relatively low volume, pre-mixed, ready-to-use, injectable formulation of nicardipine that is stable enough for clinical use, and yet provides a suitable nicardipine concentration for immediate use, without dilution, by parenteral injection.

SUMMARY

Pharmaceutical compositions of 1,4-dihydropyridine compounds having improved stability, methods of making and using them are provided. According to one embodiment, there is a pharmaceutical composition comprising a 1,4-dihydropyridine compound and a chelating agent. In another embodiment, there is a pharmaceutical composition consisting essentially of a 1,4-dihydropyridine compound, a chelating agent, and at least one of a solvent, a tonicity agent, a co-solvent, a buffering agent, or excipient. In yet another embodiment, there is a pharmaceutical composition consisting of a 1,4-dihydropyridine compound, a chelating agent, and at least one of a tonicity agent, a solvent, a co-solvent, a buffering agent, or excipient.

In one embodiment, the present disclosure is directed to pharmaceutical compositions having at least one calcium channel blocker and at least one chelating agent. Preferably, the calcium channel blocker is a DHP compound. The chelating agent is no more than about 10 weight percent of the composition.

The pharmaceutical compositions can be of various dosage forms and be used to treat various cardiovascular disorders (e.g., hypertension, coronary artery disease, angina, arrhythmia, and blood circulatory conditions). Preferably, the dosage form of the pharmaceutical compositions is a solution for injection contained in either an ampule, vial, bag or prefilled syringe. The compositions demonstrate improved stability compared to known pharmaceutical compositions containing DHPs.

Also, the pharmaceutical compositions have fewer total impurities by weight and less of a particular pyridine analog impurity when exposed to various environmental conditions.

In some embodiments, there is a sterile composition comprising at least one 1,4-dihydropyridine compound and at least one chelating agent in a single use container.

In another embodiment, there is a method of treating at least one cardiovascular disorder in a human in need thereof, the method comprising administering a therapeutically effective amount of a pharmaceutical composition comprising at least one 1,4-dihydropyridine compound and at least one chelating agent.

In yet another embodiment, there is a method of preparing a stable pharmaceutical composition of at least one 1,4-dihydropyridine compound, the method comprising providing at least one chelating agent and mixing the chelating agent with the at least one 1,4-dihydropyridine compound to form the stable pharmaceutical composition.

In still yet another embodiment, there is a method of preparing a stable pharmaceutical composition of at least one 1,4-dihydropyridine compound, the method comprising mixing an aqueous carrier with a co-solvent to form a mixture; adding and mixing a buffering agent, a base and a chelating agent to the mixture to form a buffered mixture; and adding and mixing the at least one 1,4-dihydropyridine compound to the buffered mixture to form the stable pharmaceutical composition.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

All scientific and technical terms used herein have meanings commonly used in the art unless otherwise specified. The definitions provided herein are to facilitate understanding of certain terms used frequently herein and are not meant to limit the scope of the present disclosure.

It is noted that, as used in this specification and the appended claims, the singular forms "a," "an," and "the," include plural referents unless expressly and unequivocally limited to one referent. Thus, for example, reference to "an antioxidant" includes one, two, three or more antioxidants.

As used in this specification and the appended claims, the term "or" is generally employed in its sense including "and/or" unless the content clearly dictates otherwise.

Unless defined otherwise, all technical and scientific terms used herein have the same meaning as is commonly understood by one of skill in the art to which the disclosure(s) belong. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

Compounds for use in the compositions described herein that may contain one or more asymmetric centers can thus occur as racemates and racemic mixtures, single enantiomers. The compositions are meant to comprehend all isomeric forms of such compounds.

The term "antioxidant" refers to a substance that inhibits or delays oxidation.

The term "calcium channel blocker(s)" refers to compounds that inhibit, reduce or prevent the movement of calcium into and/or within cells.

The term "chelating agent(s)" refers to compounds that react with metal ions to form a stable, water-soluble complex including those compounds that prevent or delay oxidation.

The term "composition(s)" refers to an aggregate material formed from two or more substances, ingredients or constituents; the way in which a whole or mixture is made up.

When referring to pharmaceutical drug products, a composition is often called "formulation(s)".

The term "dihydropyridine(s)" refers to molecules based upon pyridine, and the parent of a class of molecules that have been semi-saturated with two substituents replacing one double bond.

The term "dosage form(s)" refers to pharmaceutical drug products in the form in which they are marketed for use, administration or consumption, with a specific mixture of active ingredient(s) and inactive component(s) (excipients), in a particular configuration. Examples of dosage forms include without limitation, liquid, solid, semisolid, suspension, powder, crystal, paste, oral (pill, tablet, capsule, film, solution, liquid, syrup, buccal), inhalational, device (aerosol, inhaler, nebulizer, vaporizer, pen), sublingual, nasal, suppository (vaginal, rectal, urethral, nasal), parenteral (intradermal, subcutaneous, intramuscular, intraosseous, intraperitoneal, intravenous), topical (cream, gel, liniment, balm, lotion, ointment, drop, patch, ring, talc), ophthalmic and injectable.

The term "impurity" refers to a constituent, component or ingredient which impairs the purity of pharmaceutical active ingredient or pharmaceutical composition.

The term "injectable" or "injectable composition," as used herein, means a composition that can be drawn into or filled in a container and injected intravenously, subcutaneously, intramuscularly, intra-arterially, intra-cardiac, intrathecally, epidurally, intraparenchymally, intraperitoneally, intracerebroventricularly, intraventricularly, or the like into an animal.

The term "reference listed drug" refer to an approved drug product to which generic versions are compared to show that they are bioequivalent.

The term "stability" refers to capability of a pharmaceutical active ingredient or pharmaceutical composition to remain within a specific criteria or specification(s).

The term "stable", as used herein, means remaining in a state or condition that is suitable for administration to a patient and without undergoing a substantial change in the potency of the active agent in the formulation over the specified time period. In some embodiments, compositions are stable when maintained at room temperature for at least 6 months, usually at least 12 months, and generally for at least 18, 24, 36 or 48 months. In some embodiments, the compositions are also preferably stable over more extended periods of time when stored at 25° C. A substantial change in potency is one which decreases the drug concentration by more than 10% from the target concentration for the specified period of time. Unless indicated otherwise, a stable composition is one which retains at least 90% of the original amount of the 1,4-dihydropyridine compound in that state (e.g., not precipitated, degraded or adsorbed to the container) for a period of at least six months at the appropriate storage conditions.

The carriers and excipients and other components of the pharmaceutical compositions must be "pharmaceutically acceptable" in the sense of being compatible with the other ingredients of the formulation and not deleterious to the recipient thereof. Thus, the term "pharmaceutically acceptable salt" references salt forms of the active compounds which are prepared with counter ions which are non-toxic under the conditions of use and are compatible with a stable formulation. For compounds which contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. Salts derived from pharmaceutically acceptable organic non-toxic bases include salts of primary, secondary, and tertiary amines, substituted amines including naturally occurring substituted amines, cyclic amines, ethanolamine, 2-diethylaminoethanol, lysine, arginine, and histidine.

For compounds which contain relatively basic functionalities, acid addition salts can be obtained by contacting the neutral form of such compounds with a sufficient amount of the desired base, either neat or in a suitable inert solvent. Examples of "pharmaceutically acceptable acid addition salts" (i.e., salts retaining the biological effectiveness and properties of the free bases and which are not biologically or otherwise undesirable), can be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "pharmaceutically acceptable carrier or excipient" means a carrier or excipient that is useful in preparing a pharmaceutical composition that has an acceptable side-effect profile and serves to provide a medium for the storage or administration of the active component(s) under the conditions of administration for which the composition is formulated or used. The carrier or excipient is compatible with the other ingredients of the formulation and not deleterious to the recipient thereof. A "pharmaceutically acceptable carrier or excipient" as used in the specification and claims includes both one and more than one such carrier or excipient. Pharmaceutically acceptable carriers are determined in part by the particular composition being administered, as well as by the particular method used to administer the composition. Also, an excipient can perform more than one function. For example, sorbitol can act as both a tonicity agent and a co-solvent. There are a wide variety of suitable formulations of pharmaceutical compositions of the present disclosure (see, e.g., Remington's Pharmaceutical Sciences, 20th ed., 2018, supra).

The term "tonicity adjusting agents" refers to agents used to modify the osmolality of a formulation to bring it closer to the osmotic pressure of body fluids such as blood or plasma. Provided that the compositions are physiologically compatible, the compositions do not require any particular osmolality. Thus, the compositions can be hypotonic, isotonic, or hypertonic. Typically, the pharmaceutical compositions have an osmolality between about 250 to 350 mOsm/kg. The tonicity of the pharmaceutical compositions can be adjusted by adjusting the concentration of any one or more of a tonicity agent, a co-solvent, complexing agent, buffering agent, or excipient. Suitable tonicity adjusting agents include, but are not limited to, anhydrous and hydrous forms of NaCl, dextrose, sucrose, xylitol, fructose, glycerol, sorbitol, mannitol, KCl, $CaCl_2$, $MgCl_2$ or a combination thereof.

"Buffering agents" are agents used to control the pH of a formulation. A variety of buffering agents are suitable and may be used alone or together in the composition. Suitable buffering agents include, but are not limited to, acids and salts of acetate, glutamate, citrate, tartrate, benzoate, ascorbic acid, lactate, amino acids, gluconate, succinate, MES, phosphate or a combination thereof. The buffering agent can be in a concentration from 0.1 to 100 mM, inclusive, 0.1 to 0.5 mM, 0.5 to 1 mM, 1 to 5 mM, 5 to 20 mM, inclusive, 5 to 50 mM, inclusive, or 50-100 mM inclusive. In some embodiments, the tonicity agent can function as a buffering agent. In other embodiments, the buffering agent can function as a tonicity agent.

The pH of the pharmaceutical composition can be adjusted to the recited pH range or target pH by the addition of an acid or acidic salt (e.g., HCl, ascorbic acid, phosphoric acid), or base or basic salt, as appropriate. For instance, the pH may be adjusted with a base such as an alkali metal hydroxide such as NaOH, KOH, or LiOH, a phosphate, or an alkaline earth metal hydroxide, such as $Mg(OH)_2$ or $Ca(OH)_2$, or a carbonate. The buffering agent may be the acid or base form of the species which gives rise to the salt of the nicardipine.

A "co-solvent" is a solvent which is added to the formulation and assists in the solubilization of the 1,4-dihydropyridine compound(s). Co-solvents, for instance, can be selected from the group consisting of polyhydric alcohols (e.g., sorbitol, mannitol, xylitol), glycols (e.g., propylene glycol and polyethylene glycol), organic liquids (e.g., ethanol), or water. Typically, the co-solvent is in a concentration from 0.1% to 25%.

The term "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients described herein. In one embodiment, a pharmaceutical composition generally comprises a therapeutically effective amount of nicardipine, one or more buffering agents, and other ingredients as described herein.

The term "therapeutically effective amount" refers to an amount of an agent sufficient to treat or prevent acute elevations in blood pressure or induce hypotension when administered alone or as one of multiple dosages to a subject. The "therapeutically effective amount" will vary depending on the formulation, the severity of the blood pressure elevation, the age, general health condition, and weight of the subject to be treated.

The term "pre-mixed", as used herein, means a pharmaceutical composition that is already mixed from the point of pre-sale packaging and/or manufacture and does not require reconstitution or dilution before administration to a subject.

The term "single-use container" refers to a sealed pharmaceutically prepared container holding a drug product in a sterile environment that is intended to be used in a single operation of transferring the entire contents or substantially entire contents, wherein the transfer operation spans no more than 10-12 hours, but often less than 8 hours, or even 6 hours. It should be recognized that the single-use container is generally preservative-free and that if multiple transfers are attempted, they should be completed in a short duration, i.e., less than about 8-10 hours from the first breach of the sterile environment. In some aspects the single-use container may be used to administer all of its contents to one subject in need thereof. In some aspects the single-use container may be used to administer its contents to more than one subject in need thereof.

As used herein, the term "mixing" refers to admixing, contacting, blending, stirring or allowing to admix, mix, blend, stir and the like.

The term "dissolved oxygen" refers to oxygen that is found in the aqueous carrier of the compositions. Distinguished from dissolved oxygen is the headspace oxygen. As used herein, the term "headspace oxygen" refers to the oxygen that is found in the headspace volume of the sealed container comprising the composition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

The headings below are not meant to limit the disclosure in any way; embodiments under anyone heading may be used in conjunction with embodiments under any other heading.

DHP Compositions

The disclosure described herein relates to the development of pharmaceutical grade compositions or formulations in which the inclusion of a chelating agent or agents results in more stable compositions. More specifically, the present disclosure is directed to pharmaceutical compositions having at least one calcium channel blocker and at least one chelating agent. Preferably, the calcium channel blocker is a DHP compound, more preferably, one or more of nicardipine, nifedipine, nimodipine, clevidipine, amlodipine, isradipine, felodipine, nisoldipine, azelnidipine, cilnidipine, nitrendipine, aranidipine, barnidipine, benidipine, efonidipine lacidipine, lercanidipine, manidipine, nilvadipine, nitrendipine, or free bases, hydrates, solvates, crystalline polymorphs, amorphous forms, or pharmaceutically acceptable salts thereof.

The compositions can be administered by parenteral routes, including, subcutaneous, intramuscular, and intravenous routes, to a patient. The compositions can be provided in a single-use vial for injection, a multidose vial for injection or a premixed intravenous container suitable for an intravenous infusion.

DHP compounds include hydrates and solvates. The term "solvate" as used herein refers to an aggregate or complex that comprises one or more molecules of a compound of the disclosure with one or more molecules of solvent. Examples of solvents that form solvates include, but are not limited to, water, isopropanol, ethanol, methanol, DMSO, ethyl acetate, acetic acid, and ethanolamine. The term "hydrate" refers to the aggregate or complex where the solvent molecule is water. The solvent may be inorganic solvents such as for example water in which case the solvate may be a hydrate. Alternatively, the solvent may be an organic solvent, such as ethanol. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compounds of the disclosure may merely retain adventitious water or be a mixture of water plus some adventitious solvent. When referring to the DHP compound, unless otherwise specified or apparent from context, it is to be understood that the inventors are also referring to pharmaceutically acceptable salts. Examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycolic, gluconic, gulonic, succinic, arylsulfonic, e.g., p-toluenesulfonic acids, and the like.

In certain embodiments, pharmaceutical compositions of this disclosure relate to nicardipine composition for injection as a direct bolus intravenous injection or to be diluted in a suitable delivery vehicle containing dextrose, saline or a combination thereof and administered to a human subject as a bolus dose or intravenous infusion. Further, when referring to the DHP compound or particularly nicardipine, the active ingredient may not only be in the salt form, but also in the base form (e.g., free base).

In one embodiment, the pharmaceutical composition comprises 0.25 mg to 5.0 mg/mL, inclusive of nicardipine (as calculated for either nicardipine base or its hydrochloride salt) in an aqueous formulation having one or more buffering agent(s) each in a concentration from 0.1 mM to 100 mM, and a pH from about 3.5 to 5.5, inclusive, and one or more additional pharmaceutically acceptable excipients or carriers. In some embodiments, the buffering agent(s) can be any one or more salts and acids of citrate, malate, formate, succinate, acetate, propionate, histidine, carbonate, tartrate, phosphate, or 2-(N-morpholino)ethanesulfonic acid (MES). Optionally, the compositions comprise a tonicity adjusting agent and/or a co-solvent. Suitable tonicity adjusting agents include but are not limited to, dextrose or sodium chloride. Suitable co-solvents include but are not limited to, polyhydric alcohols (e.g., sorbitol, mannitol, xylitol), glycols (e.g., propylene glycol and polyethylene glycol), and ethanol in a concentration range varying from 0.1 to 25% w/v. Typically, the compositions are provided as low volume, pre-mixed, ready-to-use, bolus injectable, aqueous pharmaceutical compositions. Alternatively, the compositions may be lyophilized and reconstituted in water, saline or a pharmaceutically acceptable aqueous carrier to provide the compositions for use as a bolus injection or they can be further diluted and administered as an intravenous infusion.

Pharmaceutically acceptable salts of a DHP compound (e.g., nicardipine) include salts forms of the active compounds which are prepared with counter ions which are non-toxic under the conditions of use and are compatible with a stable formulation. For compounds which contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. Salts derived from pharmaceutically acceptable organic nontoxic bases include salts of primary, secondary, and tertiary amines, substituted amines including naturally occurring substituted amines, cyclic amines, ethanolamine, 2-diethylaminoethanol, lysine, arginine, and histidine.

Examples of pharmaceutically acceptable salts of DHP (e.g., nicardipine) are hydrochlorides, sulfates, phosphates, acetates, fumarates, maleates and tartrates. In some embodiments, the pharmaceutically acceptable salt of nicardipine is nicardipine hydrochloride.

In some embodiments, in the pharmaceutical compositions of this disclosure, the DHP compound can vary in the pharmaceutical composition from 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0 wt/wt %. The DHP compound can be in powder form before it is mixed in a suitable solvent to form an injectable DHP pharmaceutical composition.

The DHP can be made in a solution at the appropriate concentration suitable for injection and be in a solution having a pH range, in some embodiments, of from about from about 3.0, 3.1, 3.2, 3.3, 3.4, 3.5, 3.6, 3.7, 3.8, 3.9, to about 4.0. The DHP composition can have, suitable buffers, tonicity adjusting agents, pH adjusting agents, solvents, co-solvents, chelating agents to make it suitable for injection.

In one embodiment, the DHP is nicardipine hydrochloride in a 0.1 mg/mL or 0.2 mg/mL solution for intravenous administration in either dextrose or sodium chloride solution. In certain embodiments, each mL of premixed injectable I.V. solution contains 0.1 mg nicardipine hydrochloride, 48 mg dextrose hydrous, USP, 0.0192 mg anhydrous citric acid USP, and 1.92 mg sorbitol, NF.

In some embodiments, the nicardipine concentration is in a range from 0.3 mg/mL to 0.7 mg/mL; 0.4 mg/mL to 0.6 mg/mL; or 0.5 mg/mL of solution. In some embodiments, the nicardipine concentration is from 1.0 mg/mL to 0.9 mg/mL, from 0.9 mg/mL to 0.8 mg/mL, from 0.8 mg/mL to 0.7 mg/mL, from 0.7 mg/mL to 0.6 mg/mL, from 0.6 mg/mL to 0.5 mg/mL, from 0.5 mg/mL to 0.4 mg/mL, from 0.4 mg/mL to 0.3 mg/mL, 0.3 mg/mL to 0.25 mg/mL.

Hydrochloric acid and/or sodium hydroxide can be added to adjust pH to 3.7 to 4.7 of the pharmaceutical composition. In certain embodiments, each mL of premixed injectable I.V. solution contains 0.1 mg nicardipine hydrochloride, 8.6 mg sodium chloride, USP, 0.0192 mg anhydrous citric acid USP, and 1.92 mg sorbitol, NF. In various aspects, the pH of the nicardipine solution can vary from about 3.5, 3.6, 3.7, 3.8, 3.9, 4, 4.1, 4.2, 4.3, 4.4, 4.5, 4.6, to about 4.7. In one embodiment, the pH range for a nicardipine hydrochloride I.V. dosage form varies from about 3.0 to about 3.9, more specifically, from about 3.0, 3.1, 3.2, 3.3, 3.4, 3.5, 3.6, 3.7, 3.8, to about 3.9.

In various embodiments, the DHP compositions (e.g., nicardipine) described in this disclosure are in an aqueous formulation having one or more buffering agent(s) each in a concentration from 0.1 mM to 100 mM, and a pH from about 3.5 to 5.5, inclusive. For example, in some embodiments, the composition comprises a buffering agent from 0.5 mM to 50 mM in concentration and a pH more than 3.5 but less than 5.0. In some embodiments, the buffering agent(s) can be any one or more of an acid or salt of citrate, malate, formate, succinate, acetate, propionate, histidine, carbonate, tartrate, phosphate, or MES. In some embodiments, the buffering agent can be in the DHP composition in an amount of from about 0.001, 0.0015, 0.025, 0.03, 0.04, 0.05, 0.0525, 0.06, 0.07, 0.1, 0.5, 1.0, 1.5, 2.0, 2.5, 3.0, 3.5, 4.0, 4.5, to about 5.0 wt.% based on the total weight of the composition.

In some embodiments, the buffer is a single buffer selected from the group comprising acetate, citrate, succinate, and phosphate. In some embodiments, the compositions comprise two, three, four, or more different buffering agents. For example, in some embodiments, the compositions comprise two buffering agents, selected from the group consisting of acetate and citrate; acetate and phosphate; acetate and succinate; citrate and phosphate; citrate and succinate; and succinate and phosphate. In other embodiments, the compositions comprise three or more buffering agents selected from the group consisting of acetate, phosphate and succinate; citrate, phosphate and acetate; succinate, phosphate and citrate; and citrate, acetate and succinate buffering agents. In some embodiments, the buffering agent can be in powder form and added to the DHP composition to form the injectable DHP composition.

Optionally, the DHP compositions can comprise tonicity adjusting agents and/or co-solvents. In some embodiments, the tonicity adjusting agent is dextrose or sodium chloride. In some embodiments, the co-solvent is polyhydric alcohols (e.g., sorbitol, mannitol, xylitol), glycols (e.g., propylene glycol and polyethylene glycol), and ethanol, in a concentration range varying from 0.1 to 25% w/v. In some embodiment, the solvent, tonicity adjusting agent, and/or co-solvent can be in the DHP composition in an amount of from 0.1, 0.25, 0.5, 0.75, 1.0, 1.5, 2.0, 2.5, 3.0, 3.5, 4.0, 4.5, 4.8, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, to 25.0% w/v based on the total weight of the composition. Typically, the compositions are provided as low volume, pre-mixed, ready-to-use, injectable, bolus aqueous pharmaceutical compositions. In certain aspects, the injection composition of the present invention may be available as a concentrate composition to be mixed with infusion fluids such as 0.9% sodium chloride or 5% dextrose before administration to the patient, or ready to use compositions which are premixed with infusion fluids such as 0.9% sodium chloride or 5% dextrose.

In some embodiments, the formulations comprise (a) nicardipine or a pharmaceutically acceptable salt thereof, (e.g., nicardipine hydrochloride), (b) at least one buffering agent; (c) a tonicity agent; and (d) optionally a co-solvent, in which the pH of the composition is between 3.5 and 5.5.

Chelating Agents

It has been surprisingly found that the addition of chelating agent(s) to a composition comprising at least one DHP compound stabilizes it by reducing the formation of corresponding pyridine analog impurities. In some embodiments, the chelating agent is available in its pharmaceutically acceptable salts, esters, solvates, polymorphs, enantiomers or mixtures thereof. For example, EDTA is available as pharmaceutically acceptable salts or hydrated salts. The chelating agent can be in powder form before it is mixed in a suitable solvent to form an injectable DHP pharmaceutical composition.

The chelating agent can be added to the DHP pharmaceutical composition in an amount of from about 0.0001, 0.0002, 0.0003, 0.0004, 0.0008, 0.001, 0.0015, 0.025, 0.03, 0.04, 0.05, 0.06, 0.07, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, to about 10.0% by weight based on the total weight of the composition.

The chelating agents are no more than about 10 weight percent of the pharmaceutical composition and preferably include, without limitation, one or more of ethylenediaminetetraacetic acid (EDTA), ethylene glycol-bis(β-aminoethyl ether)-N,N,N',N'-tetraacetic acid (EGTA), cyanocobalamin, dimercaprol, diethylenetriaminepentaacetic acid (DTPA), (N-hydroxyethylethylenediamine-N,NT,N''-triacetic acid) (HEDTA), nitrilotriacetic acid (NTA), penicillamine, deferoxamine mesylate, and pharmaceutically acceptable salts thereof. Most preferably, the chelating agent is EDTA which is about 0.0004 weight percent to about 0.040 weight percent of the composition, for example, from about 0.0005, 0.0006, 0.0007, 0.0008, 0.0009, 0.001, 0.002, 0.003, 0.004, 0.005, 0.006, 0.007, 0.008, 0.009, 0.010, 0.020, 0.030, 0.035 to about 0.040 wt/wt %. The compositions can be any pharmaceutical dosage form including liquids, solids or suspensions; preferably, the dosage form can be an aqueous solution and, more preferably, a solution for injection contained in an ampoule, vial, bag or prefilled syringe. The pharmaceutical compositions can be used to treat various cardiovascular disorders (e.g., hypertension, coronary artery disease, angina, arrhythmia, and blood circulatory conditions).

Although many chelating agents lack inherent properties to qualify as "true antioxidant(s)," e.g., sodium metabisulfite, glutathione, cysteine, butylated hydroxytoluene, or butylated hydroxyanisole, the compositions of the present disclosure exhibited a significant reduction in the rate and extent of oxidation of the dihydropyridine ring to form the pyridine analog impurity. This is a surprising result considering that various metal chelating agents, including EDTA, have been shown to stimulate the oxidation of various molecules. See Mozziconacci, O. et al., Metal-catalyzed oxidation of protein methionine residues in human parathyroid hormone (1-24): formation of homocysteine and a novel methionine-dependent hydrolysis reaction. Molecular Pharmaceutics, (2013), 10(2), 735-755; see also, Gutteridge J. M., Ferrous ion-EDTA-stimulated phospholipid peroxidation, a reaction changing from alkoxyl-radical- to hydroxyl-radical-dependent initiation, The Biochemical Journal, 224, (1984), 697-701. As a result, the compositions encompassed by this disclosure demonstrate improved stability compared to known pharmaceutical compositions containing DHPs. Also, the pharmaceutical compositions of this disclosure have fewer total impurities by weight and less of a particular pyridine analog impurity when exposed to various environmental conditions.

The container in which the DHP compositions are held may affect the level of certain components. In certain embodiments, the DHP composition (e.g., nicardipine hydrochloride composition) can be enclosed in a single-use container. These containers can include, for example, premixed intravenous bags, bottles, vials, ampules, or syringes.

The container can have a variety of volumes. Typically, the container can have a volume of from about 10 mL to about 100 mL. In some examples, the container can have a volume of from about 1, 5, 10, 20, 30, 40 mL to about 50 mL. In other examples, the container can have a volume of from about 50, 60, 70, 80, 90 mL, 100 mL, 150 mL to about 200 mL. In still other examples, the container can have a volume of about 10 mL or about 20 mL.

The container can be made of a variety of materials. Non-limiting materials can include glass, a plastic (e.g. polyethylene, polypropylene, polyvinyl chloride, polycarbonate, etc.), the like, or a combination thereof provided that it can both prevent oxygen penetration and minimize aluminum, heavy metals and anions contamination to the composition. In certain embodiments, the container is fabricated from multilayered plastic (PL 2501, PL 2040), also known as a galaxy container, a plastic container primarily for intravenous use. Solutions are in contact with the polyethylene layer of the container and can leach out certain chemical components of the plastic in very small amounts within the expiration period.

In other aspects, the container can be fabricated from glass as a single use 10 mL vial, for example, a Type I glass vial for injectable products. In some aspects, the pharmaceutical compositions of this disclosure can also be stored in glass vials or ampules, for example, single use 10 mL glass vials or ampules.

As previously discussed, the pH range for a nicardipine hydrochloride I.V. dosage form varies from about 3.0 to about 3.9. This low pH can disrupt the plastic coating or silicon coating inside the glass container and aluminum, heavy metals and anions could leach during the shelf life of the product, especially over prolonged storage of the product. Elemental impurities monitored in the finished drug products described in this disclosure include without limitation Cd, Pb, As, Hg, Co, V, Ni, Tl, Au, Pd, Ir, Os, Rh, Ru, Se, Ag, Pt, Li, Sb, Ba, Mo, Cu, Sn, and Cr. In some embodiments, the DHP composition comprises 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, to about 5.0 ppb of these impurities. However, the levels of specific metals ions are monitored in the finished drug product units over the entire shelf life but are not quantified in the bulk Water for Injection (WFI), USP used to prepare the batch. Rather, the level of all soluble metals and any other electrolytes is measured in the bulk Water for Injection, USP via measurement of conductivity.

In some aspects, the limit for parenteral administration of the permitted daily exposure (PDE) of nicardipine HCl Injection, USP as specified in ICH Q3D Step 4 Option 2 can be about 30%. In other aspects the limit for parenteral administration of the PDE of nicardipine HCl Injection, USP as specified in ICH Q3D Step 4 Option 2 can be 100%.

Impurities

Pharmaceutical compositions comprising DHP active ingredients can be prone to photo-degradation and oxidation and thus stringent process controls of light and oxygen are required during manufacturing and storage. Ideally, it is desirable to keep the impurities as low as possible. Without wishing to be bound by a particular theory, it is believed that a reason for such degradation is that the pyridine analog impurity is a further resonance-stabilized form compared to the parent drug (i.e., DHP active ingredient) and thus the formation of this impurity is a thermodynamically favored degradation pathway. The pyridine analog impurity is the primary degradant of nicardipine and other DHP calcium channel blockers and the proposed chelating agent stabilized formulation has been shown to reduce the rate and extent of its formation; hence it is the impurity of interest in the patent application. In some embodiments, impurities from the DHP ring can be in the DHP composition in an amount from about 0.0, 0.01, 0.02, 0.03, 0.04, 0.05, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, to about 2% by weight based on the total weight of the DHP composition.

One impurity in the formulations of this disclosure is 3-{2-[benzyl(methyl)amino]ethyl} 5-methyl 2,6-dimethyl-4-(3-nitrophenyl)pyridine-3,5-dicarboxylate, which is considered a pyridine analog impurity. Additional impurities can include, for example, nicardipine monoacid (5-(Methoxycarbonyl)-2,6-dimethyl-4-(3-nitrophenyl)-1,4-dihydropyridine-3-carboxylic acid) and N-benzyl-N-methylethanolamine. In some embodiments, ranges for nicardipine impurities are set forth in Table 2 below.

TABLE 2

Impurities of Nicardipine

| Impurity | Ranges |
| --- | --- |
| Nicardipine Monoacid (5-(Methoxycarbonyl)-2,6-dimethyl-4-(3-nitrophenyl)-1,4-dihydropyridine-3-carboxylic acid) | 0.0%–0.24% |
| N-Benzyl-N-methyl-ethanolamine | 0.0%–0.74% |
| Any Unknown Impurity | 0.0%–0.24% |

Headspace Oxygen

In certain embodiments, the compositions further comprise within the container, headspace gas that includes oxygen in an amount of from about 0.5% v/v to about 5.0% v/v, or from about 0.5% v/v to about 4.0% v/v, or from about 0.5% v/v to about 3.5% v/v, from about 0.5% v/v to about 3.0% v/v, or from about 0.5% v/v to about 2.5% v/v, or from about 0.5% v/v to about 2.0% v/v, or from about 0.5% v/v to about 1.5% v/v, or from about 0.5% v/v to about 1.0% v/v, or in some cases from about 0.1% v/v to about 0.5% v/v, or from about 0.1% v/v to about 0.4% v/v, or from about 0.1% v/v to about 0.3% v/v, or from about 0.1% v/v to about 0.2% v/v. For the sake of clarity and the ease of discussion and measurement, these values are taken for the 1,4-dihydropyridine composition at the time of its manufacture ("time zero" data point), or during and up to 1 month from time zero. Additional time points beyond the 1 month from time zero data point may provide similar headspace oxygen levels.

Without wishing to be bound by a particular theory, the dissolved oxygen levels and the head space oxygen levels within a sealed container of 1,4-dihydropyridine compositions described herein may reach an equilibrium at some time point during its shelf-life. Such equilibrium may be maintained for a very short time, i.e., for a few seconds, or for a very long time, i.e., for several months. Such equilibrium may on occasion be disturbed by simple agitation. Therefore, it should be recognized that dissolved oxygen levels and headspace oxygen levels may fluctuate from one time point to another in terms of absolute numbers. However, the numbers are expected to stay within the ranges disclosed herein. Occasionally, one number (e.g., dissolved oxygen) may exceed or fall out of a certain range (e.g., from about 0.5 to about 3.0 PPM) at a 15 day time point but may fall within that range at some other time point (e.g., 30 day time point, or later). Therefore, in some aspects, the ranges, subranges, and specific data points disclosed and discussed herein are suitable for time points beyond the time zero and 1 month time points. In one aspect, the time points could be extended to from about 2 months, 3 months, 6 months, 9 months, 12 months, 15 months, 18 months, and about 24 months.

In some aspects, the total amount of oxygen in the sealed container may be an appropriate measure to evaluate the stability of the 1,4-dihydropyridine compositions herein. For example, the total amount of oxygen within the container may be arrived at by adding up the amount of dissolved oxygen in the carrier and the amount of head space oxygen. These values can also be expressed independently in separate units (i.e., dissolved oxygen as ppm and head space oxygen as % v/v). An example would be an 1,4-dihydropyridine composition that contains a dissolved oxygen level of from about 0.0 ppm to 9.0 ppm, more specifically, from about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 to about 9.0 ppm and a head space oxygen level of about 0.5% v/v to about 4.0% v/v. In certain embodiments, the total amount of oxygen within the container is expected to increase upon filling into vials due to the inherent aeration of the drug product during filling (e.g. splashing). Based on what has been seen for other drug products, the dissolved oxygen in the finished units (e.g., vials) is expected to be in the range of from about 0.0 ppm to about 7.0 ppm, more specifically, from about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9 to about 7.0 ppm.

The amount of oxygen present in the headspace of the container can be controlled by filling the headspace with an inert gas, such as nitrogen or argon. Alternatively, the head space oxygen may be controlled by vacuum operation without using an inert gas. In another aspect, the head space oxygen may be controlled by a combination of vacuum operation and inert gas overlay. In one particular aspect, the head space oxygen is controlled by repeated pulses of vacuum and inert gas overlay in tandem such that the process may start first with vacuum operation followed by inert gas overlay followed by vacuum operation. The combination of vacuum operation and inert gas overlay (or inert gas overlay and vacuum operation) is considered one pulse when both steps are used together. A typical head space control operation may comprise from one to eight pulses. Typically, there could be two, three, four, or five pulses. Each pulse could last from about one tenth of one second to five seconds or from five to fifteen seconds when conducted by automated high-speed equipment custom designed for this specific purpose. In some embodiments, the pulse may last from about 0.1 to about 2.0 seconds. In some embodiments, the pulse may last from about 0.1 to about 1.0 seconds, or from about 0.1 to about 0.4 seconds. When done using manual methods, each pulse could take up to 30-60 seconds or longer.

The U.S. Food and Drug Administration ("FDA") has designated Cardene® I.V. as a Reference Listed Drug ("RLD"). Cardene® I.V. contains nicardipine hydrochloride (2.5 mg/mL), sorbitol (48 mg/mL) to adjust tonicity and as a co-solvent/stabilizer, a buffer system comprised of citric acid monohydrate (0.525 mg/mL) and sodium hydroxide (0.09 mg/mL) to maintain the pH at about 3.0-4.0, and Water for Injection, USP (Q.S.) as the vehicle.

By comparison, the present disclosure describes DHP compositions comprising at least one chelating agent (e.g., nicardipine hydrochloride composition containing EDTA, EGTA, diethylenetriaminepentaacetic acid, or deferoxamine mesylate). Preferably, EDTA is included at a range of from about 0.004 to about 0.4 mg/mL (from about 0.0004 to about 0.04%) which is within the maximum concentration of 10% for intravenous administration of a pharmaceutical drug product per the FDA Inactive Ingredient Database. In various embodiments, more specifically, EDTA is included at a range from about 0.004, 0.005, 0.006, 0.007, 0.008, 0.008, 0.009, 0.010, 0.02, 0.03, 0.04, 0.05, 0.06, 0.07, 0.08, 0.09, 0.1, 0.2, 0.3, 0.4 mg/mL. In one particular embodiment, a composition contains nicardipine hydrochloride (2.5 mg/mL), sorbitol (48 mg/mL), citric acid monohydrate (0.525 mg/mL), sodium hydroxide (0.09 mg/mL), EDTA (0.04 mg/mL), and Water for Injection, USP (Q.S.).

During a manufacturing process, in one embodiment, dissolved oxygen levels are controlled via sparging with an inert gas. Additionally, a blanket of inert gas (e.g., nitrogen, argon, helium) can be maintained throughout manufacturing and storage to control atmospheric oxygen exposure, while an opaque container (e.g. stainless steel or amber glass, Teflon-lined vessels, plastic disposable vessels, or other vessels that shield a formulation from light) is selected to protect the formulation from exposure to light.

In some embodiments, the DHP composition is preservative-free. As used herein, preservative-free includes compositions that do not contain any preservative. Thus, the composition does not contain, for example, benzalkonium chloride, methyl, ethyl, propyl or butylparaben, benzyl alcohol, phenylethyl alcohol, or benzethonium.

In some embodiments, one or more preservatives can be incorporated into the injectable pharmaceutical composition described in this disclosure, especially in a multi-dose DHP composition. Preservatives can be introduced into a pharmaceutical solution to kill bacteria, yeast and mold. The bacteria, yeast, and mold can be introduced accidentally when multiple aliquots are withdrawn from a container which holds multiple doses of a medicament.

A number of preservatives are available which can kill or prevent the growth of commonly encountered contaminants; these contaminants include, but are not limited to the bacteria P. aeruginosa, E. coli and S. aureus; the yeast C. albicans; and the mold A. brasiliensis.

The presence of at least one preservative, in some embodiments, allows for the injectable pharmaceutical composition to be used over a period of at least 7 days, preferably 28 days or more once the container holding the composition is broached. The injectable pharmaceutical composition has a minimum broached vial antimicrobial effectiveness of 7 days and preferably a broached vial antimicrobial effectiveness of 28 days or more. The minimum duration is 7 days, after broaching, for the preservative/preservatives present to be effective and may allow for the pharmaceutical composition to be viable for use and/or treatment beyond this period. In certain embodiments, this time period is 28 days or more.

The incorporation of a preservative or preservatives within the pharmaceutical composition should not hinder the solubility of the DHP and the final compositions are still able to pass a test method complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

In some embodiments at least one preservative is present in the pharmaceutical composition and can be selected from a group comprising but not limited to: m-cresol, chlorocresol, parabens including but not limited to methylparaben, ethyl paraben, propylparaben, butylparaben, their derivatives, and salts, chlorobutanol, quaternary ammonium compounds, their derivatives, and salts including benzethonium chloride, benzalkonium chloride, boric acid, benzyl alcohol, cetylpyridinium chloride, cetrimide, phenol, phenyl ethanol, phenoxyethanol or mixtures thereof.

The preservative or preservatives are present in an amount which is effective to impart the desired preservative characteristics and allows the final composition to comply with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

Methods of Making and Use

In various embodiments, the present disclosure relates to pre-mixed, ready-to-use, injectable pharmaceutical compositions comprising a DHP or a pharmaceutically acceptable salt, hydrate or solvate thereof, at least one solvent, co-solvent and a buffering agent. The composition may further comprise a tonicity agent. The compositions are preferably isotonic.

The pharmaceutical compositions of the present application can be made by mixing an aqueous carrier, such as for example, water with a co-solvent as discussed above to form a mixture. To the mixture, a buffering agent, a base and a chelating agent can be added to form a buffered mixture. To the buffered mixture the 1,4-dihydropyridine compound can be added to form the pharmaceutical composition. The mixing can be done at temperatures from about 5° C. to about 100° C., for example, at 25° C. to 30° C.

It will be understood that, in some embodiments, the components of the pharmaceutical composition (e.g., DHP compound, chelating agent, solvent, co-solvent, buffering agent, etc.) can be mixed in any order. After, mixing and the additions of the components, the pharmaceutical composition can be sterilized, for example, by filtering it through one or more filters (e.g., 0.22 p.m sterile filters). The sterilized pharmaceutical composition can then be filled in the appropriate container (e.g., vial, ampule, etc.) and stoppered and sealed, for example, under a reduced oxygen headspace of either 5% oxygen (balance nitrogen) or 10% oxygen (balance nitrogen). In some embodiments, the pharmaceutical composition can be packaged in a pharmaceutically acceptable container, such as an intravenous bag, syringe, vial or ampule. The pH of the compositions is, in some aspects, between 3 and 7, and in other aspects, from 3.0 to 3.9.

The present disclosure also relates to methods for preparing such compositions. In this other aspect, the term "pre-mixed", as used herein, means a pharmaceutical composition that is already mixed from the point of manufacture and does not require dilution or further processing before administration. The term "pre-mixed" may also mean a pharmaceutical composition wherein the liquid solution and the active pharmaceutical ingredient are separated from the point of manufacture and in storage, such as when the solution is stored in an intravenous bag and the active pharmaceutical ingredient is lyophilized and stored in a vial that is connected to the bag, but not in fluid contact with the solution until just before administration to a patient. In various embodiments, pre-mixed injection can be a single-use, ready-to-use, iso-osmotic solution for intravenous administration. No further dilution would be required. Prior to administration, the pre-mixed injection should be visually inspected for particulate matter and discoloration prior to administration, whenever solution and container permit. A pre-mixed injection is normally a clear, colorless to yellow solution.

In many aspects, the pharmaceutical compositions are aqueous solutions that are administered by injection. Alternatively, the pharmaceutical compositions may be lyophilized and then reconstituted in a solution (e.g., sterile water for injection, dextrose, sodium chloride, etc.) for example, before intravenous administration.

Preferably, the compositions are used for the treatment of cardiovascular and cerebrovascular conditions. In one embodiment, the pharmaceutical compositions of the present disclosure comprise a cardiac medication or a pharmaceutically acceptable salt thereof. In certain embodiments, the cardiac medication is a calcium channel antagonist or a pharmaceutically acceptable salt thereof. For example, the cardiac medication is a dihydropyridine derivative or a pharmaceutically acceptable salt thereof. In various embodiments, the cardiac medication is nicardipine or a pharmaceutically acceptable salt thereof. For example, they are disclosed in, among other references, U.S. Pat. No. 3,985,758, which is incorporated herein by reference in its entirety.

In some embodiments, the pharmaceutical compositions comprise from 0.1 to 15 mg/mL nicardipine or a pharmaceutically acceptable salt thereof. For example, suitable concentrations of nicardipine or a pharmaceutically acceptable salt thereof, include, but are not limited to: 0.1-15 mg/mL, 0.1-10 mg/mL, 0.1-5 mg/mL, 0.1-3.0 mg/mL, 0.1-2.0 mg/mL, 0.1-1.0 mg/mL, 0.9 mg/mL, 0.8 mg/mL, 0.7 mg/mL, 0.6 mg/mL, 0.5 mg/mL, 0.4 mg/mL, 0.3 mg/mL, 0.2 mg/mL or 0.1 mg/mL.

Therapeutically effective amounts include dosage ranges of the DHP (e.g., nicardipine) to achieve the desired effect. In some embodiments, the dosage range for nicardipine can be from 10 mg to 120 mg per day or higher.

In some embodiments, a pharmaceutical composition of nicardipine hydrochloride is administered as an I.V. infusion of 20 mg in 200 mL (0.1 mg/mL) at an initial rate of 25mL (2.5mg) every 5 to 15 minutes, or 50 mL/hr (5 mg/hr). If the desired blood pressure reduction is not achieved at this dose, the infusion rate may be increased by 25 mL/hr (2.5 mg/hr) every 5 minutes (for rapid titration) to 15 minutes (for gradual titration) up to a maximum of 150 mL/hr (15 mg/hr), until desired blood pressure reduction is achieved. In other embodiments, following the achievement of the blood pressure goal utilizing rapid titration, the infusion rate can be decreased to 30 mL/hr (3 mg/hr).

In other embodiments, a pharmaceutical composition of nicardipine hydrochloride is administered as an I.V. infusion 40 mg in 200 mL (0.2 mg/mL) at an initial rate of 25 mL/hr (5 mg/hr). If the desired blood pressure reduction is not achieved at this dose, the infusion rate may be increased by 12.5 mL/hr (2.5 mg/hr) every 5 minutes (for rapid titration) to 15 minutes (for gradual titration) up to a maximum of 75 mL/hr (15 mg/hr), until desired blood pressure reduction is achieved. Following the achievement of the blood pressure goal utilizing rapid titration, the infusion rate can be decreased to 15 mL/hr (3 mg/hr).

In another aspect, the pharmaceutical compositions can be used to treat cardiac conditions. In many embodiments, the compositions can be used to treat conditions that are alleviated by the administration of calcium channel antagonists, such as cardiovascular and cerebrovascular conditions. Cardiovascular conditions that can be treated with the pharmaceutical compositions of the present disclosure include angina, ischemic, systemic arterial hypertension, congestive heart failure, coronary artery disease, myocardial infarction, cardiac arrhythmias, cardiomyopathies and arteriosclerosis. Cerebrovascular conditions that can be treated with the pharmaceutical compositions of the present disclosure include pulmonary hypertension, cerebral insufficiency, acute cerebral hemorrhage, and migraine. In some embodiments, the compositions are used to treat hypertension.

In certain aspects, the pharmaceutical compositions of the present disclosure also comprise at least one co-solvent. Therefore, the compositions may comprise a co-solvent, or multiple co-solvents.

In another aspect, nicardipine and its pharmaceutically acceptable salts are only slightly soluble in water. Co-solvents can help solubilize nicardipine in the aqueous solution of the pharmaceutical composition. Co-solvents are especially beneficial when a high concentration of nicardipine is present, such as in the compositions of the present disclosure. An advantage of the compositions of the present disclosure is that they have a high concentration of nicardipine, which allows the composition to be administered using a lower volume of intravenous fluid. Such compositions can be a treatment option for a greater number of patients, especially volume restricted patients.

In another embodiment, patients and medical conditions that may benefit from a higher concentration and lower fluid volume of nicardipine include, but are not limited to, the following: acute congestive cardiac failure; pediatrics; hypertensive crises in elderly patients where fluid overload is a major concern; all acute stroke areas including AIS, ICH and SAH to control blood pressure; controlled hypotension during surgical procedures including cardiothoracic surgery (CABG, coarctation of the aorta, etc.), spinal surgeries, and head and neck surgeries; and neurosurgery for the control of breakthrough hypertension post carotid endarterectomy, traumatic brain injury and potential treatment of hypertension and vasospasm.

In another aspect, in addition to enhancing solubility, co-solvents and chelating agents enhance the stability of the pharmaceutical compositions. Furthermore, changes may be made to the concentration of co-solvents and chelating agents in the pharmaceutical compositions in order to adjust the tonicity of the pharmaceutical compositions. Pharmaceutically acceptable co-solvents are known in the art and are commercially available. Useful co-solvents include, for example, polyethylene glycol (PEG), propylene glycol (PG), ethanol, sorbitol or water. In some aspects, the co-solvent concentration is 0.1-10% weight/volume percent, which will depend on the pH of the composition. In other aspects, the co-solvent concentration is 0.1-5%. In certain aspects, the co-solvent concentration is 0.1-2%. In various embodiments, co-solvents for the pharmaceutical compositions are propylene glycol and sorbitol. In certain aspects, the concentration of propylene glycol is 0.1-2%. In other aspects, the concentration of sorbitol is 0.1-4.8%. In yet other aspects, the concentration of sorbitol is 0.1-2%.

In addition, the pharmaceutical compositions of this disclosure can comprise at least a buffering agent and in some embodiments, the compositions may comprise multiple buffering agents. The pharmaceutical compositions of the present disclosure are preferably close to physiological pH in order to minimize the incidence of phlebitis upon administration. However, the pH of the pharmaceutical composition also affects the solubility and stability of nicardipine in the composition. Generally, as the pH of the pharmaceutical composition increases, the aqueous solubility of nicardipine decreases. As a result, it is difficult to solubilize nicardipine close to a physiological pH. In addition, the composition should have sufficient buffering capacity such that the solution does not precipitate upon dilution with blood when administered.

Buffering agents are used to adjust the pH of the pharmaceutical compositions in this alternative aspect as well. The pH of the compositions is, in some cases, between 3.5 and 7.5. In other aspects, the pH of the compositions is between 4 and 6. In some aspects, the pH of the compositions is between 4.0 and 5.5. Most preferably, the pH of the composition is between 3.7 and 4.7.

In many aspects, typical buffering agents include acetate, glutamate, citrate, tartrate, benzoate, lactate, histidine or other amino acids, gluconate, phosphate and succinate. In certain aspects, the concentration of a buffering agent can be 1-100 mM. In other aspects, the buffering agent concentration is 1-50 mM. In yet other aspects, the buffering agent concentration is 25-35 mM.

In another aspect, the pharmaceutical compositions of the present disclosure are isotonic, i.e., in the range of 270-328 mOsm/kg. However, the compositions may have a tonicity in the range of 250-350 mOsm/kg. Therefore, the compositions may be either slightly hypotonic, 250-269 mOsm/kg, or slightly hypertonic, 329-350 mOsm/kg. In various embodiments, the tonicity of the pharmaceutical compositions is rendered isotonic by adjusting the concentration of any one or more of co-solvent, chelating agent and buffering agent in the solution.

In another aspect, the pharmaceutical compositions of the present disclosure may further comprise a tonicity agent. However, the compositions may further comprise multiple tonicity agents. Tonicity agents are well known in the art and commercially available. Useful tonicity agents include, for example, sodium chloride and dextrose. In several aspects, the tonicity agent is sodium chloride. In other aspects, the tonicity agent concentration is 1-200 mM. In many aspects, the tonicity agent concentration is 75-125 mM. In other aspects, the tonicity agent concentration is 90-110 mM.

The pharmaceutical compositions of the present disclosure are preferably packaged in pharmaceutically acceptable containers in many aspects. Pharmaceutically acceptable containers include intravenous bags, bottles, vials, and syringes. In certain embodiments, the containers include intravenous bags and syringes, which can be polymer-based, and vials and intravenous bottles, which can be made of glass. In some embodiments, the components of the container that come into contact with the pharmaceutical composition do not contain polyvinylchloride (PVC). In various aspects, the container is an intravenous bag that does not have any PVC containing components in contact with the pharmaceutical composition. It is also desirable to protect the pharmaceutical compositions from light. Therefore, the container may, optionally, further comprise a light barrier. In certain embodiments, the light barrier can be an aluminum over pouch.

In many aspects, the present disclosure also provides methods for preparing sterile pharmaceutical compositions. Examples of suitable procedures for producing sterile pharmaceutical drug products include, but are not limited to, terminal moist heat sterilization, ethylene oxide, radiation (i.e., gamma and electron beam), and aseptic processing techniques. Any one of these sterilization procedures can be used to produce the sterile pharmaceutical compositions described herein.

Sterile pharmaceutical compositions may also be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the compositions can be sterile filled into a container to avoid the heat stress of terminal sterilization.

These and other aspects of the present application will be further appreciated upon consideration of the following Examples, which are intended to illustrate certain particular embodiments of the application, but they are not intended to limit its scope, as defined by the claims.

EXAMPLES

Example

A composition having the same components and quantity of components as Cardene® I.V. was prepared as a control composition to evaluate the efficacy of a chelating agent (EDTA) to improve the stability of the composition and is listed as comparative example 1.

Comparative Example 1

Each mL of the formulation contains:

| | |
|---|---|
| Nicardipine Hydrochloride | 2.5 mg |
| Sorbitol | 48 mg |

-continued

| | |
|---|---|
| Citric Acid Monohydrate | 0.525 mg |
| Sodium Hydroxide | 0.09 mg |
| Water for Injection | Q.S. to 1 mL |

Example 1

Each mL of the formulation contains:

| | |
|---|---|
| Nicardipine Hydrochloride | 2.5 mg |
| Sorbitol | 48 mg |
| Citric Acid Monohydrate | 0.525 mg |
| Sodium Hydroxide | 0.09 mg |
| EDTA | 0.04 mg |
| Water for Injection | Q.S. to 1 mL |

The compositions of Comparative Example 1 and Example 1 were prepared using the same compounding process, and filled into the same container closure system (10 mL amber Type I glass vials with 20 mm rubber stoppers and aluminum cap/seals) with the same headspace gas composition (5% oxygen, balance nitrogen) before placing the compositions on stability for evaluation such that the only difference was the presence of EDTA in the two compositions. Additionally, in another stability study, Example 1, was filled into the same container closure system with a 10% oxygen (balance nitrogen) in the headspace.

More specifically, a 2-Liter stainless steel compounding vessel was charged with Water for Injection, USP and mixing via an overhead mixer at 450 RPM was initiated along with nitrogen sparging and nitrogen blanketing. After approximately 30 minutes, the dissolved oxygen content was verified to be below the limit of not more than 3.0 mg/L using a Mettler Toledo Seven2go™ Pro(DO) Dissolved Oxygen Meter, Model S9 with InLab® Optiox Electrode. The formula weight of sorbitol was then added and mixed for 5-10 minutes. The formula weight of citric acid monohydrate was then added and mixed for 10-15 minutes followed by the addition of the formula weight of sodium hydroxide and mixing for 5-10 minutes. After adding the formula weight of edetate disodium to the compounding vessel, the bulk solution in the vessel was mixed for 10-15 minutes. The bulk solution was then heated to 25-30° C. and nicardipine hydrochloride was added and mixed for 50-60 minutes before the bulk solution was cooled to 20-25° C. and brought to 90-95% of the final weight with pre-sparged Water for Injection, USP from a side vessel. After mixing for 5-10 minutes the pH was verified (Thermo Scientific Orion pH Meter, Model Star A211). Optionally, the pH can be adjusted with, e.g., citric acid and/or sodium hydroxide to a desired value, before the bulk solution is brought to the final weight with pre-sparged Water for Injection, USP from the side vessel. The final pH and dissolved oxygen content were verified after mixing for 5-10 minutes. The product was continuously filtered through two 0.22 μm sterile filters in series. The filtered bulk solution was filled into 10-mL Type I, Amber glass vials. The filled units were stoppered and sealed under a reduced oxygen headspace of either 5% oxygen (balance nitrogen) or 10% oxygen (balance nitrogen).

The stability of the compositions was assessed by monitoring various parameters such as pH, assay, and impurity profile (i.e., total impurities and the pyridine analog impurity) under different storage conditions expressed as relative retention time. In some embodiments, the vials containing nicardipine hydrochloride compositions were inverted during storage conditions. For nicardipine assay determination, an isocratic reverse phase HPLC-UV method using C18 column was used. The mobile phase is a mixture of citrate buffer, trimethylamine and acetonitrile. For pyridine analog and total impurity determination, a gradient reverse phase HPLC-UV method using C18 column was used. The method employs a binary gradient of citrate buffer with 0.1% trimethylamine and acetonitrile. The detection wavelength for both methods is 254 nm. The relative retention time (RRT) is the ratio of the retention time of analyte peak relative to that of another used as a reference obtained under identical conditions. Results are summarized in Tables 3, 4, 5, 6, 7, and 8, wherein the measured nicardipine pyridine analog impurity is 3-{2-[benzyl(methyl)amino]ethyl} 5-methyl 2,6-dimethyl-4-(3-nitrophenyl)pyridine-3,5-dicarboxylate.

Stability data of Nicardipine Hydrochloride Injection formulations with 5% headspace oxygen at different storage conditions are listed in Tables 3, 4 and 5.

TABLE 3

Storage Condition: 40° C./75% RH (Inverted)

| Batch | pH | | | | % Assay | | | | % Pyridine Analog Impurity[1] (RRT 1.10) | | | | % Total Impurities | | | |
|---|---|---|---|---|---|---|---|---|---|---|---|---|---|---|---|---|
| Time (month) | T0 | T1 | T2 | T3 | T0 | T1 | T2 | T3 | T0 | T1 | T2 | T3 | T0 | T1 | T2 | T3 |
| Comparative | 3.81 | 3.80 | 3.83 | 3.93 | 96.7 | 98.8 | 95.7 | 95.0 | 0.05 | 1.07 | 1.66 | 2.17 | 0.05 | 1.35 | 2.57 | 3.51 |
| Example 1 | | | | | 97.8 | 98.1 | 96.0 | 96.4 | 0.05 | 1.08 | 1.70 | 1.06 | 0.05 | 1.36 | 2.59 | 2.34 |
| Example 1 | 3.80 | 3.81 | 3.84 | 3.88 | 100.0 | 102.0 | 98.9 | 99.1 | 0.04 | 0.42 | 0.46 | 0.68 | 0.04 | 0.71 | 1.37 | 2.08 |
| | | | | | 99.7 | 102.3 | 98.6 | 98.9 | 0.03 | 0.42 | 0.48 | 0.67 | 0.03 | 0.72 | 1.37 | 2.05 |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate

TABLE 4

| Batch | pH | | | | | % Assay | | | | |
|---|---|---|---|---|---|---|---|---|---|---|
| Time (month) | T0 | T1 | T2 | T3 | T6 | T0 | T1 | T2 | T3 | T6 |
| Comparative Example 1 | 3.81 | 3.80 | 3.79 | 3.83 | 3.81 | 96.7 | 99.0 | 97.7 | 97.9 | 95.8 |
|  |  |  |  |  |  | 97.8 | 100.3 | 95.8 | 98.2 | 96.9 |
| Example 1 | 3.80 | 3.82 | 3.81 | 3.85 | 3.82 | 100.0 | 103.5 | 100.3 | 100.6 | 101.7 |
|  |  |  |  |  |  | 99.7 | 104.6 | 98.6 | 100.5 | 101.7 |

Storage Condition: 30° C./65% RH (Inverted)

| Batch | % Pyridine Analog Impurity[1] (RRT 1.10) | | | | | % Total Impurities | | | | |
|---|---|---|---|---|---|---|---|---|---|---|
| Time (month) | T0 | T1 | T2 | T3 | T6 | T0 | T1 | T2 | T3 | T6 |
| Comparative Example 1 | 0.05 | 0.45 | 0.78 | 0.98 | 2.16 | 0.05 | 0.50 | 0.80 | 1.33 | 2.94 |
| Example 1 | 0.05 | 0.57 | 0.77 | 0.47 | 0.32 | 0.05 | 0.62 | 0.83 | 0.82 | 1.05 |
| Example 1 | 0.04 | 0.24 | 0.28 | 0.33 | 0.67 | 0.04 | 0.29 | 0.42 | 0.70 | 1.45 |
|  | 0.03 | 0.28 | 0.28 | 0.31 | 0.68 | 0.03 | 0.33 | 0.34 | 0.65 | 1.47 |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate

TABLE 5

Storage Condition: 25° C./60% RH (Inverted)

| Batch | pH | | | % Assay | | | % Pyridine Analog Impurity[1] (RRT 1.10) | | | % Total Impurities | | |
|---|---|---|---|---|---|---|---|---|---|---|---|---|
| Time (month) | T0 | T3 | T6 | T0 | T3 | T6 | T0 | T3 | T6 | T0 | T3 | T6 |
| Comparative Example 1 | 3.81 | 3.82 | 3.81 | 96.7 | 98.7 | 96.7 | 0.05 | 0.68 | 1.75 | 0.05 | 0.83 | 2.11 |
|  |  |  |  | 97.8 | 98.5 | 96.3 | 0.05 | 0.65 | 1.82 | 0.05 | 0.81 | 2.22 |
| Example 1 | 3.80 | 3.86 | 3.82 | 100.0 | 101.1 | 99.0 | 0.04 | 0.29 | 0.75 | 0.04 | 0.44 | 1.17 |
|  |  |  |  | 99.7 | 101.2 | 99.1 | 0.03 | 0.30 | 0.63 | 0.03 | 0.41 | 1.04 |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate Stability data of EDTA stabilized Nicardipine Hydrochloride Injection formulation (Example 1) with different headspace oxygen levels at different storage conditions are listed in Tables 6, 7 and 8.

TABLE 6

Storage Condition: 40° C./75% RH (Inverted)

| Parameter | Assay (% LC) | | | | % Pyridine Analog[1] (RRT 1.10) | | | | % Total Impurities | | | |
|---|---|---|---|---|---|---|---|---|---|---|---|---|
| Time Point | T0 | T1 | T2 | T3 | T0 | T1 | T2 | T3 | T0 | T1 | T2 | T3 |
| 10% Oxygen | 100.1 | 103.8 | 99.3 | 97.9 | ND | 0.40 | 0.47 | 0.81 | 0.01 | 0.72 | 1.28 | 2.14 |
|  |  | 103.7 | 99.6 |  |  | 0.40 | 0.48 | 0.76 |  | 0.72 | 1.31 | 2.11 |
| 5% Oxygen |  | 103.1 | NT | 97.4 |  | 0.36 | NT | 0.50 |  | 0.67 | NT | 1.77 |
|  |  | 102.8 | NT |  |  | 0.38 |  | 0.51 |  | 0.65 |  | 1.80 |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate ND = Not Detected, NT = Not Tested.

TABLE 7

Storage Condition: 30° C./65% RH

| Parameter | Assay (% LC) | | | | % Pyridine Analog[1] (RRT 1.10) | | | | % Total Impurities | | | |
|---|---|---|---|---|---|---|---|---|---|---|---|---|
| Time Point | T0 | T1 | T3 | T6 | T0 | T1 | T3 | T6 | T0 | T1 | T3 | T6 |
| 10% | 100.1 | 104.6 | 99.7 | 100.5 | ND | 0.24 | 0.31 | 0.41 | 0.01 | 0.35 | 0.68 | 1.23 |
| Oxygen | | 104.5 | | 101.1 | | 0.23 | 0.30 | 0.47 | | 0.34 | 0.64 | 1.30 |
| 5% | | 103.8 | 97.6 | 99.0 | | 0.20 | 0.23 | 0.53 | | 0.30 | 0.61 | 1.36 |
| Oxygen | | 103.6 | | 99.6 | | 0.18 | 0.21 | 0.51 | | 0.29 | 0.59 | 1.34 |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate
ND = Not Detected, NT = Not Tested.

TABLE 8

Storage Condition: 25° C./60% RH

| Parameter | Assay (% LC) | | | % Pyridine Analog[1] (RRT 1.10) | | | % Total Impurities | | |
|---|---|---|---|---|---|---|---|---|---|
| Time Point | T0 | T3 | T6 | T0 | T3 | T6 | T0 | T3 | T6 |
| 10% | 100.1 | 98.8 | 99.7 | ND | 0.17 | 0.26 | 0.01 | 0.29 | 0.74 |
| Oxygen | | | 100.5 | | | 0.27 | | 0.26 | 0.70 |
| 5% | | 98.2 | 99.4 | | 0.13 | 0.39 | | 0.59 | 0.87 |
| Oxygen | | | 99.3 | | | 0.29 | | 0.33 | 0.78 |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate
ND = Not Detected, NT = Not Tested.

Example 2

A composition having the same components and quantity of components as Cardene® I.V. was prepared as a control composition to evaluate the efficacy of additional chelating agents (EGTA, diethylenetriaminepentaacetic acid, and deferoxamine mesylate) to improve the stability of the composition and is listed as comparative example 2.

Comparative Example 2

Each mL of the control formulation contains:

| | |
|---|---|
| Nicardipine Hydrochloride | 2.5 mg |
| Sorbitol | 48 mg |
| Citric Acid Monohydrate | 0.525 mg |
| Sodium Hydroxide | 0.09 mg |
| Water for Injection | Q.S. to 1 mL |

Example 2-A

Each mL of the formulation contains:

| | |
|---|---|
| Nicardipine Hydrochloride | 2.5 mg |
| Sorbitol | 48 mg |
| Citric Acid Monohydrate | 0.525 mg |
| Sodium Hydroxide | 0.09 mg |
| EGTA | 0.04 mg |
| Water for Injection | Q.S. to 1 mL |

Example 2-B

Each mL of the formulation contains:

| | |
|---|---|
| Nicardipine Hydrochloride | 2.5 mg |
| Sorbitol | 48 mg |
| Citric Acid Monohydrate | 0.525 mg |
| Sodium Hydroxide | 0.09 mg |
| Diethylenetriaminepentaacetic acid | 0.04 mg |
| Water for Injection | Q.S. to 1 mL |

Example 2-C

| | |
|---|---|
| Nicardipine Hydrochloride | 2.5 mg |
| Sorbitol | 48 mg |
| Citric Acid Monohydrate | 0.525 mg |
| Sodium Hydroxide | 0.09 mg |
| Deferoxamine Mesylate | 0.04 mg |
| Water for Injection | Q.S. to 1 mL |

The compositions of Comparative Example 2 and Example 2-A, Example 2-B, and Example 2-C were prepared using the same compounding process, and filled into the same container closure system (10 mL amber Type I glass vials with 20 mm rubber stoppers and aluminum cap/seals) with the same headspace gas composition (5% oxygen, balance nitrogen) before placing the compositions on stability for evaluation such that the only difference was the chelating agent present in the compositions.

More specifically, a 1-Liter stainless steel or glass compounding vessel was charged with Water for Injection, USP and mixing was initiated at 350 RPM was initiated along with nitrogen sparging and nitrogen blanketing. After approximately 30 minutes, the dissolved oxygen content was verified to be below the limit of not more than 3.0 mg/L using a Mettler Toledo Seven2go™ Pro(DO) Dissolved Oxygen Meter, Model S9 with InLab® Optiox Electrode. The formula weight of sorbitol was then added and mixed for 5-10 minutes. The formula weight of citric acid monohydrate was then added and mixed for 10-15 minutes followed by the addition of the formula weight of sodium hydroxide and mixing for 5-10 minutes. After adding the formula weight of the chelating agent (EGTA, Diethylenetriaminepentaacetic acid, or Deferoxamine Mesylate) to the compounding vessel, the bulk solution in the vessel was mixed for 10-15 minutes. The bulk solution was then heated to 25-30° C. and nicardipine hydrochloride was added and mixed for 50-60 minutes before the bulk solution was cooled to 20-25° C. and brought to 90-95% of the final weight with pre-sparged Water for Injection, USP from a side vessel. After mixing for 5-10 minutes the pH was verified (Thermo Scientific Orion pH Meter, Model Star A211) and adjusted, as necessary, for example, using citric acid or sodium hydroxide, before the bulk solution was brought to the final weight with pre-sparged Water for Injection, USP from the side vessel. The final pH and dissolved oxygen content were verified after mixing for 5-10 minutes. The product was continuously filtered through two 0.22 μm sterile filters in series. The filtered bulk solution was filled into 10-mL Type I, Amber glass vials. The filled units were stoppered and sealed under a reduced oxygen headspace of 5% oxygen (balance nitrogen).

The stability of the compositions was assessed by monitoring various parameters such as assay and impurity profile (i.e., total impurities and the pyridine analog impurity) under different accelerated storage conditions. For nicardipine assay determination, an isocratic reverse phase HPLC-UV method using C18 column was used. The mobile phase is a mixture of citrate buffer, trimethylamine and acetonitrile. For pyridine analog and total impurity determination, a gradient reverse phase HPLC-UV method using C18 column was used. The method employs a binary gradient of citrate buffer with 0.1% trimethylamine and acetonitrile. The detection wavelength for both methods is 254 nm. The results are summarized in Tables 9, 10, 11 and 12.

Stability data of Nicardipine Hydrochloride Injection formulations with alternate chelating agents at different storage conditions:

TABLE 9

| | \% Assay | | \% Pyridine Analog Impurity[1] (RRT 1.10) | | \% Total Impurities | |
|---|---|---|---|---|---|---|
| Batch | | | | | | |
| Time (month) | T0 | T1 | T0 | T1 | T0 | T1 |
| Comparative | 101.2 | 79.7 | 0.10 | 10.36 | 0.10 | 12.53 |
| Example 2 | 101.6 | | 0.09 | | 0.09 | |
| Example 2-A | 99.8 | 84.1 | 0.08 | 12.73 | 0.08 | 15.05 |
| | 99.9 | | 0.09 | | 0.09 | |
| Example 2-B | 101.0 | 97.8 | 0.08 | 1.46 | 0.08 | 3.39 |
| | 102.2 | | 0.06 | | 0.06 | |
| Example 2-C | 101.1 | 98.1 | 0.03 | 1.06 | 0.03 | 3.10 |
| | 101.1 | | 0.03 | | 0.03 | |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate.

TABLE 10

Storage Condition: 40° C./75% RH (Inverted)

| | \% Assay | | | | \% Pyridine Analog Impurity[1] (RRT 1.10) | | | | \% Total Impurities | | | |
|---|---|---|---|---|---|---|---|---|---|---|---|---|
| Batch | | | | | | | | | | | | |
| Time (month) | T0 | T1 | T2 | T3 | T0 | T1 | T2 | T3 | T0 | T1 | T2 | T3 |
| Comparative | 101.2 | 102.1 | 94.3 | 9.59 | 0.10 | 0.46 | 4.35 | 0.29 | 0.10 | 0.63 | 4.85 | 1.07 |
| Example 2 | 101.6 | 100.8 | 97.9 | 9.86 | 0.09 | 1.59 | 0.64 | 1.15 | 0.09 | 1.63 | 1.10 | 1.92 |
| Example 2-A | 99.8 | 99.4 | 92.8 | 92.4 | 0.08 | 1.53 | 3.87 | 7.17 | 0.08 | 1.53 | 4.32 | 8.13 |
| | 99.9 | 98.7 | 93.1 | 92.2 | 0.09 | 1.62 | 4.04 | 6.85 | 0.09 | 1.62 | 4.56 | 7.77 |
| Example 2-B | 101.0 | 102.1 | 96.0 | 97.6 | 0.08 | 0.54 | 0.70 | 1.13 | 0.08 | 0.65 | 1.10 | 1.92 |
| | 102.2 | 102.2 | 98.9 | 99.4 | 0.06 | 0.39 | 0.73 | 1.13 | 0.06 | 0.44 | 1.16 | 1.90 |
| Example 2-C | 101.1 | 102.1 | 94.9 | 96.0 | 0.03 | 0.30 | 0.34 | 0.63 | 0.03 | 0.46 | 0.79 | 1.36 |
| | 101.1 | 102.2 | 98.9 | 98.9 | 0.03 | 0.26 | 0.36 | 0.29 | 0.03 | 0.30 | 0.80 | 1.05 |

[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate

TABLE 11

| Formulation/ Chelating Agent | Sample # | Assay T = 0 | Assay T = 1 | Assay T = 2 | Assay T = 3 | % Pyridine Impurity[1] T = 0 | % Pyridine Impurity[1] T = 1 | % Pyridine Impurity[1] T = 2 | % Pyridine Impurity[1] T = 3 | % Total Impurities T = 0 | % Total Impurities T = 1 | % Total Impurities T = 2 | % Total Impurities T = 3 |
|---|---|---|---|---|---|---|---|---|---|---|---|---|---|
| Comparative Example 2 | 1 | 101.2 | 102.8 | 99.2 | 100.9 | 0.10 | 0.07 | 0.09 | 0.07 | 0.10 | 0.07 | 0.24 | 0.28 |
| None (Control) | 2 | 101.6 | 102.4 | 98.7 | 100.2 | 0.09 | 0.10 | 0.10 | 0.08 | 0.09 | 0.10 | 0.23 | 0.27 |
| Example 2-A | 1 | 99.8 | 101.5 | 98.6 | 97.7 | 0.08 | 0.19 | 0.15 | 0.14 | 0.08 | 0.19 | 0.28 | 0.35 |
|  | 2 | 99.9 | 100.8 | 98.7 | 98.0 | 0.09 | 0.16 | 0.16 | 0.15 | 0.09 | 0.16 | 0.31 | 0.36 |
| Example 2-B | 1 | 101.0 | 102.8 | 100.5 | 101.1 | 0.08 | 0.22 | 0.45 | 0.6 | 0.08 | 0.22 | 0.58 | 0.83 |
|  | 2 | 102.2 | 102.8 | 98.1 | 99.3 | 0.06 | 0.22 | 0.40 | 0.56 | 0.06 | 0.22 | 0.53 | 0.76 |
| Example 2-C | 1 | 101.1 | 102.6 | 101.5 | 101.3 | 0.03 | 0.09 | 0.1 | 0.12 | 0.03 | 0.09 | 0.24 | 0.31 |
|  | 2 | 101.1 | 102.4 | 98.5 | 99.3 | 0.03 | NT | 0.12 | 0.08 | 0.03 | NT | 0.26 | 0.27 |

Storage Condition: 30° C./65% RH (Inverted)

NT = Not tested
[1]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate

TABLE 12

| Formulation/ Chelating Agent | Sample # | Assay T = 0 | Assay T = 1 | Assay T = 2 | Assay T = 3 | % Pyridine Impurity[2] T = 0 | % Pyridine Impurity[2] T = 1 | % Pyridine Impurity[2] T = 2 | % Pyridine Impurity[2] T = 3 | % Total Impurities T = 0 | % Total Impurities T = 1 | % Total Impurities T = 2 | % Total Impurities T = 3 |
|---|---|---|---|---|---|---|---|---|---|---|---|---|---|
| Comparative Example 2 | 1 | 101.2 | NT | NT | 98.0 | 0.10 | NT | NT | 0.10 | 0.10 | NT | NT | 0.21 |
| None (Control) | 2 | 101.6 | NT | NT | 97.8 | 0.09 | NT | NT | 0.17 | 0.09 | NT | NT | 0.28 |
| Example 2-A | 1 | 99.8 | NT | NT | 96.5 | 0.08 | NT | NT | 0.08 | 0.08 | NT | NT | 0.19 |
|  | 2 | 99.9 | NT | NT | 96.5 | 0.09 | NT | NT | 0.14 | 0.09 | NT | NT | 0.34 |
| Example 2-B | 1 | 101.0 | NT | NT | 97.7 | 0.08 | NT | NT | 0.07 | 0.08 | NT | NT | 0.20 |
|  | 2 | 102.2 | NT | NT | 97.7 | 0.06 | NT | NT | 0.07 | 0.06 | NT | NT | 0.18 |
| Example 2-C | 1 | 101.1 | NT | NT | 98.0 | 0.03 | NT | NT | 0.10 | 0.03 | NT | NT | 0.21 |
|  | 2 | 101.1 | NT | NT | 97.8 | 0.03 | NT | NT | 0.17 | 0.03 | NT | NT | 0.28 |

Storage Condition: 25° C./60% RH (Inverted)

NT = Not Tested
[2]Nicardipine Pyridine Analog Impurity is 3-{2-[benzyl(methyl)amino]ethyl} 5-methyl 2,6-dimethyl-4-(3-nitrophenyl)pyridine-3,5-dicarboxylate Discussion of the Results The chelating agent stabilized formulations (Example 1, Example 2-B, Example 2-C) demonstrated significantly improved stability under various storage conditions. In contrast, the control formulations without chelating agents (Comparative Example 1 and Comparative Example 2) had significantly more impurities at accelerated conditions within 3 months despite having the same oxygen controls in the headspace (headspace gas composition 5% oxygen, balance nitrogen). Additionally, impurity profile inconsistencies were only observed with Comparative Example 1 and Comparative Example 2 and were not observed in any of the formulations stabilized by the inclusion of the different chelating agents (Example 1, Example 2-A, Example 2-B, Example 2-C).

In summary, the addition of a chelating agent enhanced the stability of the DHP composition by decreasing the amount of total impurities, including the pyridine analog impurity, while also preventing container discrimination (i.e., vial-to-vial variability).

As evidenced by the Examples set forth herein, DHP compositions containing at least one chelating agent provide several advantages over previously known DHP compositions. One advantage is the chelating agent (e.g., EDTA, diethylenetriaminepentaacetic acid, deferoxamine mesylate) stabilized the DHP active ingredient (e.g., nicardipine hydrochloride) composition by reducing the rate and extent of impurity formation, including the pyridine analog impurity, under accelerated, intermediate, and long-term conditions. Another advantage is the DHP compositions containing a chelating agent exhibited an improved stability profile over a wider range of oxygen content in the headspace of a vial during storage. This provides a significant advantage during manufacture of DHP pharmaceutical compositions as the need for very stringent manufacturing control systems to displace oxygen in the headspace of the vial with an inert gas is reduced. A third advantage is the addition of a chelating agent (e.g., EDTA, EGTA, diethylenetriaminepentaacetic acid, deferoxamine mesylate) to a DHP pharmaceutical composition eliminates inconsistency in the rate and extent of formation of the pyridine analog impurity, generating a uniform drug product quality profile in comparison to DHP product with no chelating agent. As the pyridine analog impurity is believed to be the major degradant for all 1,4-dihydropyridine class drug products, it is expected that DHP compositions, in general, containing one or more chelating agents will have similar improved impurity and stability profiles.

Finally, a fourth advantage is the DHP pharmaceutical drug products comprising one or more chelating agents are expected to demonstrate improved product quality as a result of an improved impurity profile during the products' shelf life while meeting the same safety and efficacy standards as DHP pharmaceutical drug products which do not contain a chelating agent.

Since modifications will be apparent to those of skill in the art, it is intended that this disclosure be limited only by the scope of the appended claims.

What is claimed is:

1. A pharmaceutical composition comprising nicardipine hydrochloride in an amount of 0.1 weight percent to 5.0 weight percent, a co-solvent comprising sorbitol, mannitol, xylitol, propylene glycol, polyethylene glycol, ethanol, water or a combination thereof, the co-solvent in an amount that is 0.1 to 5 weight percent of the composition, a buffering agent comprising citric acid, anhydrous citric acid, citric acid monohydrate, sodium hydroxide or a combination thereof, the buffering agent in an amount that is 0.01 to 5.0 weight percent of the composition, and a chelating agent in an amount of 0.004 weight percent to 10 weight percent of the composition, wherein the chelating agent is ethylenediaminetetraacetic acid (EDTA), ethylene glycol-bis(β-aminoethyl ether)-N,N,N',N'-tetraacetic acid (EGTA), diethylenetriaminepentaacetic acid (DTPA), deferoxamine mesylate or free bases, hydrates, solvates, crystalline polymorphs, amorphous forms or pharmaceutically acceptable salts thereof.

2. The pharmaceutical composition of claim 1, wherein the chelating agent is also an antioxidant.

3. The pharmaceutical composition of claim 1, wherein the chelating agent is in the composition in an amount of 0.01 weight percent to 10 weight percent.

4. The pharmaceutical composition of claim 1, wherein the EDTA is edetate disodium (EDTA disodium), ethylene glycol tetraacetic acid (EGTA), diethylenetriaminepentaacetic acid (DTPA) or deferoxamine mesylate is about 0.004 weight percent to about 0.04 weight percent of the composition and the nicardipine hydrochloride is in the composition in an amount of 0.2 weight percent to 5.0 weight percent.

5. The pharmaceutical composition of claim 3, wherein (i) the composition comprises less than 2.08 weight percent total impurities after storing the composition in an atmosphere comprising 5 percent oxygen at 40° C. and 75 percent relative humidity for 3 months, or (ii) the composition comprises 0.01 weight percent to 2.08 weight percent total impurities after storing the composition in an atmosphere comprising 5 percent oxygen at 40° C. and 75 percent relative humidity for 3 months.

6. The pharmaceutical composition of claim 5, wherein (i) the total impurities comprise less than about 0.68 weight percent 3-{2-[benzyl(methyl)amino]ethyl} 5-methyl 2,6-dimethyl-4-(3-nitrophenyl)pyridine-3,5-dicarboxylate; or (ii) the total impurities comprise 0.01 weight percent to 0.68 weight percent 3-{2-[benzyl(methyl)amino]ethyl} 5-methyl 2,6-dimethyl -4-(3-nitrophenyl)pyridine-3,5-dicarboxylate.

7. The pharmaceutical composition of claim 3, wherein (i) the composition comprises less than 1.17 weight percent total impurities after storing the composition in an atmosphere comprising 5 percent oxygen at 25° C. and 60 percent relative humidity for 6 months;
or (ii) the composition comprises 0.01 weight percent to 1.17 weight percent total impurities after storing the composition in an atmosphere comprising 5 percent oxygen at 25° C. and 60 percent relative humidity for 6 months.

8. The pharmaceutical composition of claim 4, wherein (i) the composition comprises no more than 2.14 weight percent total impurities after storing the composition in an atmosphere comprising 10 percent oxygen at 40° C. and 75 percent relative humidity for 3 months; or (ii) the composition comprises 0.01 weight percent to 2.14 weight percent total impurities after storing the composition in an atmosphere comprising 10 percent oxygen at 40° C. and 75 percent relative humidity for 3 months.

9. The pharmaceutical composition of claim 8, wherein (i) the total impurities comprise no more than about 0.81 weight percent 3-{2-[benzyl(methyl)amino]ethyl} 5-methyl 2,6-dimethyl-4-(3-nitrophenyl)pyridine-3,5-dicarboxylate; or (ii) the total impurities comprise 0.01 weight percent to 0.81 weight percent 3-{2-[benzyl(methyl)amino]ethyl} 5-methyl 2,6-dimethyl-4-(3-nitrophenyl)pyridine-3,5-dicarboxylate.

10. The pharmaceutical composition of claim 4, wherein (i) the composition comprises no more than 1.30 weight percent total impurities after storing the composition in an atmosphere comprising 10 percent oxygen at 30° C. and 65 percent relative humidity for 6 months; or (ii) the composition comprises 0.01 weight percent to 1.30 weight percent total impurities after storing the composition in an atmosphere comprising 10 percent oxygen at 30° C. and 65 percent relative humidity for 6 months.

11. The pharmaceutical composition of claim 10, wherein (i) the total impurities comprise no more than about 0.47 percent 3-{2-[benzyl(methyl)amino]ethyl} 5-methyl 2,6-dimethyl-4-(3-nitrophenyl)pyridine-3,5-dicarboxylate; or (ii) the total impurities comprise 0.01 weight percent to 0.47 percent 3-{2-[benzyl(methyl)amino]ethyl} 5-methyl 2,6-dimethyl-4-(3-nitrophenyl)pyridine-3,5-dicarboxylate.

12. The pharmaceutical composition of claim 4, wherein (i) the composition comprises no more than 0.74 weight percent total impurities after storing the composition in an atmosphere comprising 10 percent oxygen at 25° C. and 60 percent relative humidity for 6 months; or (ii) the composition comprises 0.01 weight percent to 0.74 weight percent total impurities after storing the composition in an atmosphere comprising 10 percent oxygen at 25° C. and 60 percent relative humidity for 6 months.

13. The pharmaceutical composition of claim 12, wherein (i) the total impurities comprise no more than about 0.27 weight percent 3-{2-[benzyl(methyl)amino]ethyl} 5-methyl 2,6-dimethyl-4-(3-nitrophenyl)pyridine-3,5-dicarboxylate; or (ii) the total impurities comprise 0.01 weight percent to 0.27 weight percent 3-{2-[benzyl(methyl)amino]ethyl} 5-methyl 2,6-dimethyl-4-(3-nitrophenyl)pyridine-3,5-dicarboxylate.

14. The pharmaceutical composition of claim 4, wherein (i) the composition comprises no more than 7.77 weight percent total impurities after storing the composition in an atmosphere comprising 5 percent oxygen at 40° C. and 75 percent relative humidity for 3 months, and the chelating agent is ethylene glycol tetraacetic acid (EGTA) in an amount that is 0.04 weight percent of the composition; or (ii) the composition comprises 0.01 weight percent to 8.13 weight percent total impurities after storing the composition in an atmosphere comprising 5 percent oxygen at 40° C. and 75 percent relative humidity for 3 months, and the chelating agent is ethylene glycol tetraacetic acid (EGTA) in an amount that is 0.04 weight percent of the composition.

15. The pharmaceutical composition of claim 14, wherein (i) the total impurities comprise no more than about 6.85 weight percent 3-{2-[benzyl(methyl)amino]ethyl} 5-methyl 2,6-dimethyl-4-(3-nitrophenyl)pyridine-3,5-dicarboxylate; or (ii) the total impurities comprise 0.01 weight percent to 6.85 weight percent 3-{2-[benzyl(methyl)amino]ethyl} 5-methyl 2,6-dimethyl-4-(3-nitrophenyl)pyridine-3,5-dicarboxylate.

16. The pharmaceutical composition of claim 4, wherein (i) the composition comprises no more than 1.90 weight percent total impurities after storing the composition in an atmosphere comprising 5 percent oxygen at 40° C. and 75 percent relative humidity for 3 months, and the chelating agent is diethylenetriaminepentaacetic acid (DTPA) in an amount that is 0.04 weight percent of the composition; or (ii) the composition comprises 0.01 weight percent to 1.90 weight percent total impurities after storing the composition in an atmosphere comprising 5 percent oxygen at 40° C. and 75 percent relative humidity for 3 months, and the chelating agent is diethylenetriaminepentaacetic acid (DTPA) in an amount that is 0.04 weight percent of the composition.

17. The pharmaceutical composition of claim 4, wherein (i) the composition comprises no more than 1.36 weight percent total impurities after storing the composition in an atmosphere comprising 5 percent oxygen at 40° C. and 75 percent relative humidity for 3 months, and the chelating agent is deferoxamine mesylate in an amount that is 0.04 weight percent of the composition; or (ii) the composition comprises 0.01 weight percent to 1.36 weight percent total impurities after storing the composition in an atmosphere comprising 5 percent oxygen at 40° C. and 75 percent relative humidity for 3 months and the chelating agent is deferoxamine mesylate in an amount that is 0.04 weight percent of the composition.

18. The pharmaceutical composition of claim 17, wherein (i) the total impurities comprise no more than about 0.63 weight percent 3-{2-[benzyl(methyl)amino]ethyl} 5-methyl 2,6-dimethyl-4-(3-nitrophenyl)pyridine-3,5-dicarboxylate; or (ii) the total impurities comprise 0.01 weight percent to 0.63 weight percent 3-{2-[benzyl(methyl)amino]ethyl} 5-methyl 2,6-dimethyl-4-(3-nitrophenyl)pyridine-3,5-dicarboxylate.

19. The pharmaceutical composition of claim 1, further comprising an isotonicity agent.

20. The pharmaceutical composition of claim 19, wherein the tonicity agent comprises sodium hydroxide.

21. The pharmaceutical composition of claim 1, wherein the pharmaceutical composition has a pH of about 3.5 to about 4.0.

22. The pharmaceutical composition of claim 1, wherein the pharmaceutical composition comprises one chelating agent selected from ethylene glycol-bis(β-aminoethyl ether)-N,N,N',N'-tetraacetic acid (EGTA), diethylenetriaminepentaacetic acid (DTPA), deferoxamine mesylate or free bases, hydrates, solvates, crystalline polymorphs, amorphous forms or pharmaceutically acceptable salts thereof.

23. A pharmaceutical composition comprising a 1,4-dihydropyridine compound comprising nicardipine in an amount of 2.5 mg/mL of the composition and a chelating agent in an amount of 0.04 mg/mL of the composition, wherein the chelating agent is edetate disodium (EDTA disodium), ethylene glycol tetraacetic acid (EGTA), diethylenetriaminepentaacetic acid (DTPA) or deferoxamine mesylate.

24. The pharmaceutical composition of claim 23, further comprising a pH adjustment agent.

25. The pharmaceutical composition of claim 24, wherein the pH adjustment agent comprises sodium hydroxide.

26. The pharmaceutical composition of claim 24, wherein the composition comprises nicardipine hydrochloride in an amount that is 0.25 weight percent, sorbitol in an amount that is 4.8 weight percent, citric acid monohydrate in an amount that is 0.0525 weight percent, sodium hydroxide in an amount that is 0.009 weight percent and the chelating agent in an amount that is 0.004 weight percent based on a total weight of the composition.

27. A pharmaceutical composition consisting essentially of nicardipine hydrochloride in an amount from about 0.2 weight percent to about 5.0 weight percent, a chelating agent in an amount from about 0.004 weight percent to about 0.04 weight percent of the composition, a buffering agent, a solvent and a co-solvent, wherein the chelating agent is ethylenediaminetetraacetic acid (EDTA), ethylene glycol-bis(β-aminoethyl ether) -N,N,N',N'-tetraacetic acid (EGTA), diethylenetriaminepentaacetic acid (DTPA), deferoxamine mesylate or free bases, hydrates, solvates, crystalline polymorphs, amorphous forms or pharmaceutically acceptable salts thereof.

28. The pharmaceutical composition of claim 27, wherein the buffering agent is citric acid, anhydrous citric acid, citric acid monohydrate, sodium hydroxide or a combination thereof, the co-solvent is sorbitol, mannitol, xylitol, propylene glycol, polyethylene glycol, ethanol, water or a combination thereof.

29. The pharmaceutical composition of claim 27, wherein the solvent is water.

30. The pharmaceutical composition of claim 27, wherein the co-solvent is sorbitol, mannitol, xylitol, propylene glycol, polyethylene glycol, ethanol or a combination thereof, the co-solvent in an amount that is 0.1 to 5 weight percent of the composition, the buffering agent is citric acid, anhydrous citric acid, citric acid monohydrate, sodium hydroxide or a combination thereof, the buffering agent in an amount that is 0.01 to 5.0 weight percent of the composition and the solvent is water.

* * * * *